United States Patent [19]

Ekwall

[11] Patent Number: 5,683,427

[45] Date of Patent: Nov. 4, 1997

[54] ELECTROPHYSIOLOGICAL STIMULATOR WITH VARIABLE STIMULATION PULSE

[75] Inventor: Christer Ekwall, Spånga, Sweden

[73] Assignee: Pacesetter AB, Solna, Sweden

[21] Appl. No.: 673,094

[22] Filed: Jul. 1, 1996

[30] Foreign Application Priority Data

Jul. 10, 1995 [SE] Sweden .................. 9502534-2

[51] Int. Cl.[6] .................................................. A61N 1/365
[52] U.S. Cl. ................................................ 607/11; 607/28
[58] Field of Search ............................ 607/17, 20, 28, 607/11

[56] References Cited

U.S. PATENT DOCUMENTS 4,757,815  7/1988  Strandberg et al. .
5,302,643  4/1994  Roline et al. ............................. 607/28
5,549,652  8/1996  McClure et al. ........................ 607/28

FOREIGN PATENT DOCUMENTS 0 307 093  3/1989  European Pat. Off. .
0 504 935  9/1992  European Pat. Off. .
0 640 359  3/1995  European Pat. Off. .

*Primary Examiner*—William E. Kamm
*Assistant Examiner*—Kennedy J. Schaetzle
*Attorney, Agent, or Firm*—Hill, Steadman & Simpson

[57] ABSTRACT

A heart stimulator has a pulse generator which periodically emits stimulation pulses, least one electrode connectable to the pulse generator and to the heart for transmitting said pulses to the heart and a respiration monitor for monitoring the respiration of the pacemaker user. The heart stimulator adapts the energy to be delivered in a stimulation pulse in response to the information acquired by the respiration monitor which indicates the current stage in the user's respiration cycle.

46 Claims, 1 Drawing Sheet

ELECTROPHYSIOLOGICAL STIMULATOR WITH VARIABLE STIMULATION PULSE

BACKGROUND OF THE INVENTION

1. Field of the Invention

The present invention relates to heart stimulators, for the stimulation of the hearts, having a pulse generator periodically producing stimulation pulses and at least one electrode means connectable to the pulse generator and to the heart for transmitting said pulses to the heart.

2. Description of the Prior Art

Pacemakers are known which measure the respiration rate of the user and vary the interval between stimulation pulses according to the respiration rate such that an increase in the respiration rate, which generally corresponds to an increase in the activity of the user, causes an increase in the stimulation pulse rate. An example of such a pacemaker is disclosed in U.S. Pat. No. 4,757,815.

Further pacemakers are known which attempt to reduce to a minimum the energy delivered in each stimulation pulse in order to extend the life of the pacemaker battery. These pacemakers, known as autocapture pacemakers, use adjustment algorithms to determine the minimum stimulation energy level. In order to ensure capture, the stimulation pulse energy is then set at a value which is 50%–100% greater than the minimum stimulation pulse energy. The respiration of the user, however, interferes with the correct functioning of these units by continuously varying the shape of the chest, which causes temporary, non-linear variations in the stimulation impedance. This means that the stimulation pulse energy required for successful capture varies during the breathing cycle. Current algorithms do not take into account at which point in the respiration cycle the stimulation pulse occurs. This means that occasionally even a stimulation pulse containing pulse energy which is 100% greater than the minimum stimulation pulse energy is insufficient to result in a capture. In this case, current algorithms automatically increase the pulse energy for the next pulse. This pulse, however, may be unnecessarily powerful and hence waste energy because it is quite possible that, due to changes in the shape of the chest caused by respiration, the stimulation impedance may have in the meantime dropped to a lower value.

It is possible to measure the stimulation impedance directly, for example by transmitting a pulse of sufficiently low amplitude so that it cannot stimulate the heart and measuring the strength of the returning signal. Such a method, however, uses energy and is also subject to errors caused by the return signal being masked by noise from normal electrical activity in the user's body.

SUMMARY OF THE INVENTION

It is an object of the present invention to provide a heart stimulator of the above-mentioned kind which can vary the stimulation pulse energy, in order, for example, to conserve energy, without being subject to errors caused by noise from normal electrical activity in the user's body.

In accordance with the invention, this object is achieved in a heart stimulator which monitors the user's respiration cycle to indirectly determine the stimulation impedance and which then modifies the stimulation pulse energy dependent on the indirectly measured impedance so as to achieve heart stimulation with minimum energy consumption.

DESCRIPTION OF THE PREFERRED EMBODIMENTS

Figure 1A:
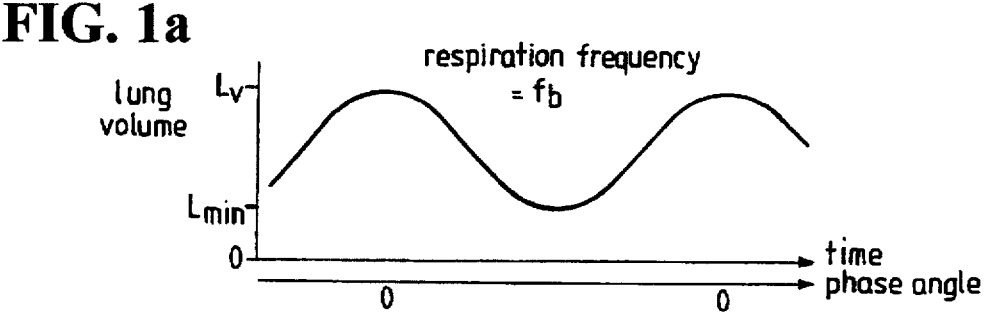
FIG. 1 shows a schematic illustration of chest volume and stimulation impedance amplitude variations and the variation in simulation pulse energy required during the respiration cycle of a heart stimulator user.
Figure 1B:
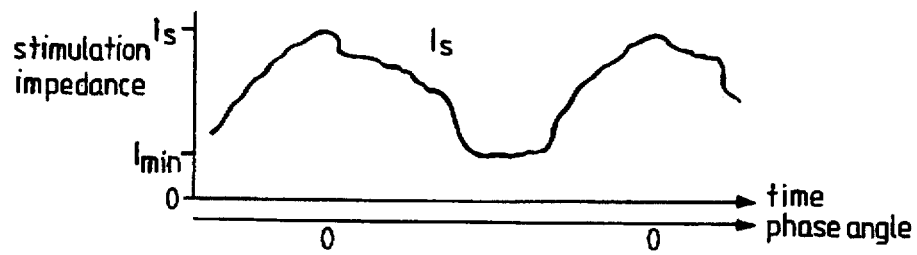
Figure 1C:
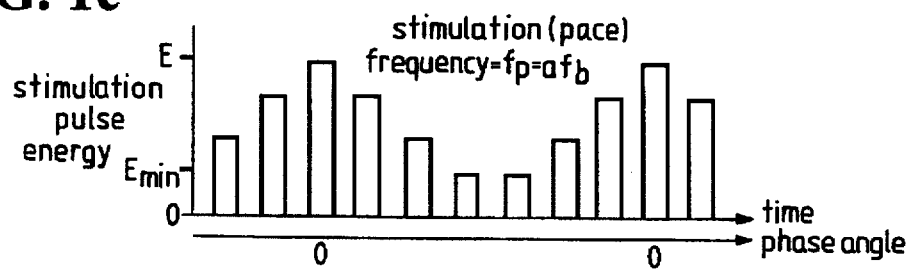

FIG. 1 shows in a simplified form how the stimulation impedance Is, and hence the minimum stimulation pulse energy varies throughout a respiration cycle. In this case stimulation impedance Is at a maximum when inhalation and hence lung volume Lv is at a maximum and stimulation impedance Is becomes smaller in a non-linear manner as air is exhaled, and vice versa. FIG. 1 also shows that the minimum stimulation pulse energy Emin required is proportional to stimulation impedance. Although the variation in stimulation impedance is non-linear, it is regular and the stimulation impedances measured at any particular stage or phase angle in consecutive respiration cycles will not vary much if the respiration rate is nearly constant.

Figure 2:
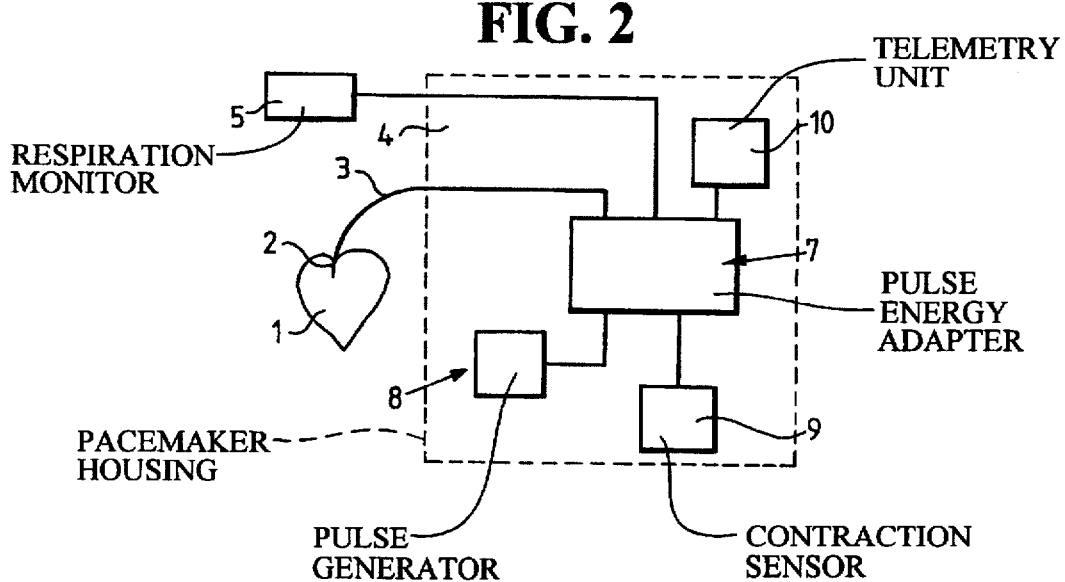
FIG. 2 is a schematic diagram of a heart stimulator constructed in accordance with the present invention.

FIG. 2 shows a heart 1 which contains an electrode 2 connectable by electrode cable 3 to a pulse energy adapter 7 inside a pacemaker housing 4. A respiration monitor 5, either contained within or separate from the pacemaker housing 4, monitors the respiration cycle and produces a respiration cycle signal. The respiration cycle signal could be based on elapsed time since, for example, the detection of the start of inhalation (which corresponds to the beginning of a respiration cycle), and the elapsed time could therefore represent the stage in the respiration cycle that the stimulator user has reached (the momentary respiration cycle phase angle). An example of a time based system could be that respiration monitor 5 measures chest pressure, which falls to a minimum when exhalation nears completion and starts to rise again when inhalation commences. The respiration monitor 5 can be programmed or contain circuitry to recognize this trough (curve inflection) and produce a start of inhalation signal. The adapter 7 can use this signal to calculate respiration rate and the stage in the respiration cycle that the stimulator user has reached. As described above, each stage in the respiration cycle that the stimulator user has reached has an associated stimulation impedance and, as described below, the adapter 7 uses the stimulation impedance associated with the stage in the respiration cycle that the stimulator user has reached to determine the required stimulation energy.

It is also possible that the respiration cycle signal could be based on the measured momentary amplitude of a parameter which varies throughout the respiration cycle. In this case the respiration cycle signal would represent the amount of inhalation or exhalation. For example, in the case where the respiration monitor 5 measures chest pressure, it can send an amplitude signal to the adapter 7, either when interrogated by the adapter 7 or continuously. Each chest pressure has an associated stimulation impedance and, in a similar manner to that described later for respiration cycle phase angle, the adapter 7 uses the associated stimulation impedance to determine the required stimulation energy. It is possible that a chest pressure amplitude has two associated stimulation impedances—a first one for inhalation and a second for exhalation. In this case adapter 7 must analyze the amplitude signal to determine if the amplitude is increasing, which would represent inhalation, or decreasing, which would represent exhalation.

There are many parameters which change in a repeatable manner during respiration and which can be used to represent the respiration cycle. A non-exhaustive list of such parameters includes lung volume, chest pressure, chest circumference, blood oxygen level, QRS signal amplitude, stimulation impedance and air, velocity, but any parameter which has a consistent relationship with the respiration cycle can be used.

The respiration monitor 5 can be any suitable electrical transducer which can measure, for example, voltage, current, resistance or impedance, or any electromechanical transducer which can measure, for example, volume, pressure, strain, torque, bending, stretching, temperature or sound, or any suitable electrochemical transducer which can measure, for example, the blood oxygen level.

During one complete respiration cycle, the parameter measured by the respiration monitor 5 will vary from a maximum value, which could correspond to when inhalation stops, to a minimum value which could correspond to when exhalation stops. For the best possible accuracy in calculating the required stimulation energy, the parameter to be measured should be chosen such that the relationship between the amplitude of the chosen parameter and the amplitude of stimulation impedance is consistent and repeatable, that is, if the stimulation impedance is recorded several times for a particular amplitude of the chosen parameter at a particular respiration rate, then the stimulation impedance should be approximately the same every time.

In a first embodiment of the invention, the respiration monitor 5 is an ultrasonic transducer, mounted in the patient chest, and it measures lung volume. The respiration monitor 5 is connected to the adapter 7 and emits an electrical signal which is proportional to the chest pressure to the adapter 7. The adapter 7 processes the incoming signal to determine when the lung volume has reached a maximum and starts to decrease. This corresponds to the end of inhalation and the beginning of exhalation. By recording the time between consecutive maximum values, the adapter 7 can calculate respiration frequency ($f_b$) and hence calculate when the next respiration cycle should begin and the current stage in the respiration cycle (the momentary respiration cycle phase angle) of the patient.

In use, the adapter 7 determines the required stimulation pulsing rate ($f_p$) in the manner which is usual for pacemakers and calculates when the next pulse is due. Before delivering or during delivery of the pulse, the adapter 7 determines the momentary respiration cycle phase angle. In order to reduce circuitry requirements, the respiration cycle can be divided into a number of sectors and a common stimulation energy requirement can be established for all the phase angles in a particular sector. For brevity in the following description the expression "phase angle" will be understood as also meaning "sector" as described above. The adapter 7 then calculates or looks up in a look-up table the stimulation energy required for the momentary respiration cycle phase angle and commands the pulse generator 8 to deliver the required pulse. The adapter 7 is connected to a telemetry unit 10 which communicates with an extracorporeal programmer (not shown) to enable the adapter 7 to be reprogrammed and to transmit output data.

In a second embodiment of the invention, instead of calculating the momentary respiration cycle phase angle, the adapter 7 has a look-up table which contains a series of respiration monitoring means signal amplitudes, for example a series of lung volume amplitudes, and a corresponding series of required stimulation energies. Alternatively, the adapter 7 can be programmed with an equation to calculate the stimulation required for a particular respiration monitoring means signal amplitude. When a stimulation pulse is to be delivered, the adapter looks up or calculates the required stimulation pulse energy using the momentary amplitude of the respiration monitoring means signal and then commands pulse generator 8 to deliver the required pulse.

In a further embodiment of the invention, the evoked response is sensed and evaluated by measurement of a physiological parameter associated with the contraction by a contraction sensor 9, either contained within or separate from the pacemaker housing 4. If a contraction is sensed within the programmable or calculated response time period, that is, the period following a stimulation pulse in which a cardiac event initiated by the pulse would normally be expected to take place, then a counter for that stage in the respiration cycle is incremented by one. Each time there is a successful contraction on stimulation for that particular stage in the respiration cycle the counter is incremented. After the counter reaches a predetermined number the stimulation energy value for that stage in the respiration cycle is reduced by a predetermined amount which can be a discrete value or a percentage of the actual stimulation energy, thus leading to a reduced energy consumption. The counter is subsequently reset to zero.

If, however, there is no contraction sensed then it is assumed that the stimulation energy was insufficient and the value in the look-up table for the stimulation energy required at that stage in the respiration cycle is incremented by an amount, which can be a discrete value or a percentage of the actual stimulation energy, and the counter for that stage in the respiration cycle is reset to zero. Thus each time no contraction is sensed for a particular stage in the respiration cycle, the stimulation pulse will be slightly more powerful the next time the same stage in the respiration cycle occurs and eventually the pulse will be sufficiently powerful to cause a contraction. It is possible that no contraction would be sensed because of the sensor 9 malfunctioning or the contraction signal being masked by other signals. This could lead to a continuous, unnecessary incrementation in the stimulation energy which, apart from wasting energy, could lead to dangerous side-effects. Therefore it would be advisable for the adapter 7 to set a maximum limit for the strength of a stimulation pulse at a given stage in the respiration cycle. Preferably the maximum limit would be made proportional to the stimulation energy calculated for one or more of the stages in the respiration cycle neighboring the given stage in the respiration cycle.

In another embodiment of the invention, the respiration monitor 5 only operates intermittently, for example for 1 or 2-minutes every hour, or for 1 minute every day or any other period. The choice of the operating period depends, inter alia, on the symptoms of the patient, the length of time the pacemaker and leads have been implanted and the stability of the pacing system. During this operating period the stimulation impedance is measured in the following way. The output capacitors of the pulse generator 8 are charged to their maximum voltage and when a stimulation pulse is required they are discharged for the maximum time programmed or calculated by the adapter 7. By measuring the voltage in the output capacitors after the pulse has been discharged it is possible to calculate the energy dissipated in the pulse and hence the stimulation impedance.

The adapter 7 records each stimulation impedance against the stage in the respiration cycle or respiration signal amplitude. At the end of the operating period the adapter 7 determines the maximum stimulation impedance, which usually occurs when lung volume is at its greatest amplitude. If, during the operating period, a stimulation impedance was measured at the time when lung volume was at its greatest amplitude, then this impedance value, if it is indeed the largest measured value, is henceforth used for calculating the required stimulation energy. If another measured stimulation impedance value is greater, then that one is used instead. If, during the operating period, no stimulation impedance was measured at the time when lung volume was at its greatest amplitude, then a theoretical stimulation impedance for this time is calculated by statistical analysis of the recorded values. If this theoretical stimulation impedance is greater than any of the measured stimulation impedances then it is henceforth used for calculating the required stimulation energy. If another measured stimulation impedance value is greater than the theoretical stimulation impedance then that one is used instead. In this way the stimulation pulse energy should be always sufficient to achieve capture. Although the stimulation pulse energy will often be higher than necessary to achieve capture, the operation of the pacemaker over time will still use less energy than the prior art devices and will not require as much computing power as the aforementioned embodiments.

The change in stimulation energy can be achieved by varying the pulse amplitude. Another way of varying stimulation energy is to vary the pulse duration. A further way of varying stimulation energy is to increase the number of pulses in a stimulation and to vary their number and/or amplitude and/or duration and/or timing.

Although modifications and changes may be suggested by those skilled in the art, it is the intention of the inventor to embody within the patent warranted hereon all changes and modifications as reasonably and properly come within the scope of his contribution to the art.

I claim as my invention:

1. A heart stimulator for stimulating a heart of a human subject, said subject having a respiration cycle with a plurality of respiration stages, said heart stimulator comprising:

a pulse generator which emits successive stimulation pulses, each stimulation pulse having an energy associated therewith;

electrode means connected to said pulse generator and implantable in said heart for transmitting said pulses in vivo to said heart;

respiration monitoring means for monitoring the respiration cycle of said subject for determining a current stage of said subject in said respiration cycle; and adapter means, connected to said respiration monitor means, for adapting the energy of a stimulation pulse as a function of the stage in the respiration cycle determined by said respiration monitoring means.

2. A heart stimulator as claimed in claim 1 wherein said respiration monitoring means comprises at least one transducer selected from the group consisting of electrical transducers, electromechanical transducers and electrochemical transducers.

3. A heart stimulator as claimed in claim 1 wherein said respiration monitoring means comprises means for directly measuring a momentary lung volume of said subject.

4. A heart stimulator as claimed in claim 1 wherein said respiration monitoring means comprises means for indirectly measuring a momentary lung volume of said subject.

5. A heart stimulator as claimed in claim 1 wherein said respiration cycle comprises at least two stages, each having a different stimulation pulse energy requirement, wherein said respiration monitoring means comprises means for generating a signal identifying which stage of said respiration cycle constitutes said current stage, and wherein said adapter means comprises means for adapting the energy of a stimulation pulse dependent on the stage of the respiration cycle identified as the current stage by said respiration monitoring means.

6. A heart stimulator as claimed in claim 5 wherein said adapter means includes a look-up table of values for stimulation pulse energies respectively required for each sector of said respiration cycle, and means for accessing said table to select the stimulation pulse energy associated with the sector of said respiration cycle identified by said respiration monitoring means.

7. A heart stimulator as claimed in claim 1 wherein said adapter means comprises means for changing an amplitude of a stimulation pulse for adapting the energy of that stimulation pulse to the current stage in the respiration cycle determined by said respiration monitoring means.

8. A heart stimulator as claimed in claim 1 wherein said adapter means comprises means for changing a pulse duration of a stimulation pulse for adapting the energy of that stimulation pulse to the current stage in the respiration cycle determined by said respiration monitoring means.

9. A heart stimulator as claimed in claim 1 wherein said pulse generator comprises means for emitting successive stimulation pulses each comprised of a stimulation complex of at least two pulses having a timing relation therebetween.

10. A heart stimulator as claimed in claim 9 wherein said adapter means comprises means for changing the timing relation dependent on the current stage in the respiration cycle determined by said respiration monitoring means.

11. A heart stimulator as claimed in claim 9 wherein said adapter means comprises means for changing an amplitude of said pulses dependent on the current stage in the respiration cycle determined by said respiration monitoring means.

12. A heart stimulator as claimed in claim 1 wherein each stimulation pulse having an appropriate energy produces an evoked response in said heart within a response time period following that stimulation pulse, and said heart stimulator further comprising means for detecting whether each stimulation pulse has produced said evoked response within said response time period.

13. A heart stimulator as claimed in claim 12 wherein said adapter means comprises means for increasing the energy of a next stimulation pulse by a predetermined amount relative to an energy of a preceding pulse if said preceding pulse did not produce an evoked response.

14. A heart stimulator as claimed in claim 12 wherein said adapter means comprises means for increasing the energy of a next stimulation pulse by a programmable amount relative to an energy of a preceding pulse if said preceding pulse did not produce an evoked response.

15. A heart stimulator as claimed in claim 12 wherein said adapter means comprises means for increasing the energy of a next stimulation pulse by a predetermined percentage relative to an energy of a preceding pulse if said preceding pulse did not produce an evoked response.

16. A heart stimulator as claimed in claim 12 wherein said adapter means comprises means for increasing the energy of a next stimulation pulse by a programmable percentage relative to an energy of a preceding pulse if said preceding pulse did not produce an evoked response.

17. A heart stimulator as claimed in claim 12 wherein said adapter means comprises means for identifying and storing the energy associated with each stimulation pulse with respect to the stage in the respiration cycle in which that stimulation pulse was emitted, means for storing a stored stimulation pulse energy for each respiration cycle stage and for normally causing each stimulation pulse emitted during a respective respiration cycle stage to have said stored stimulation pulse energy, and means for decreasing the stimulation pulse energy of a next stimulation pulse by a predetermined amount, thereby emitting a decreased energy pulse, if all of a predetermined number of previous stimulation pulses emitted in previous occurrences of said respective stage have produced an evoked response.

18. A heart stimulator as claimed in claim 17 wherein said adapter means comprises means for successively increasing the energy of respective stimulation pulses, following said decreased energy pulse, by a predetermined amount relative to the energy of said decreased energy pulse, if said decreased energy pulse did not produce an evoked response, until an evoked response is detected.

19. A heart stimulator as claimed in claim 12 wherein said adapter means comprises means for identifying and storing the energy associated with each stimulation pulse with respect to the stage in the respiration cycle in which that stimulation pulse was emitted, means for storing a stored stimulation pulse energy for each respiration cycle stage and for normally causing each stimulation pulse emitted during a respective respiration cycle stage to have said stored stimulation pulse energy, and means for decreasing the stimulation pulse energy of a next stimulation pulse by a programmable amount, thereby emitting a decreased energy pulse, if all of a programmable number of previous stimulation pulses emitted in previous occurrences of said respective stage have produced an evoked response.

20. A heart stimulator as claimed in claim 19 wherein said adapter means comprises means for successively increasing the energy of respective stimulation pulses, following said decreased energy pulse, by a programmable amount relative to the energy of said decreased energy pulse, if said decreased energy pulse did not produce an evoked response, until an evoked response is detected.

21. A heart stimulator as claimed in claim 12 wherein said adapter means comprises means for identifying and storing the energy associated with each stimulation pulse with respect to the stage in the respiration cycle in which that stimulation pulse was emitted, means for storing a stored stimulation pulse energy for each respiration cycle stage and for normally causing each stimulation pulse emitted during a respective respiration cycle stage to have said stored stimulation pulse energy, and means for decreasing the stimulation pulse energy of a next stimulation pulse by a predetermined percentage, thereby emitting a decreased energy pulse, if all of a predetermined number of previous stimulation pulses emitted in previous occurrences of said respective stage have produced an evoked response.

22. A heart stimulator as claimed in claim 21 wherein said adapter means comprises means for successively increasing the energy of respective stimulation pulses, following said decreased energy pulse, by a predetermined percentage relative to the energy of said decreased energy pulse, if said decreased energy pulse did not produce an evoked response, until an evoked response is detected.

23. A heart stimulator as claimed in claim 12 wherein said adapter means comprises means for identifying and storing the energy associated with each stimulation pulse with respect to the stage in the respiration cycle in which that stimulation pulse was emitted, means for storing a stored stimulation pulse energy for each respiration cycle stage and for normally causing each stimulation pulse emitted during a respective respiration cycle stage to have said stored stimulation pulse energy, and means for decreasing the stimulation pulse energy of a next stimulation pulse by a programmable percentage, thereby emitting a decreased energy pulse, if all of a programmable number of previous stimulation pulses emitted in previous occurrences of said respective stage have produced an evoked response.

24. A heart stimulator as claimed in claim 23 wherein said adapter means comprises means for successively increasing the energy of respective stimulation pulses, following said decreased energy pulse, by a programmable percentage relative to the energy of said decreased energy pulse, if said decreased energy pulse did not produce an evoked response, until an evoked response is detected.

25. A method for stimulating a heart of a human subject, said subject having a respiration cycle with a plurality of respiration stages, said method comprising the steps of:

emitting successive stimulation pulses, each stimulation pulse having an energy associated therewith;

transmitting said pulses in vivo to said heart;

monitoring the respiration cycle of said subject for determining a current stage of said subject in said respiration cycle; and adapting the energy of a stimulation pulse as a function of the stage in the respiration cycle determined by said monitoring of the respiration cycle.

26. A method as claimed in claim 25 wherein the step of monitoring the respiration cycle comprises directly measuring a momentary lung volume of said subject.

27. A method as claimed in claim 25 wherein the step of monitoring the respiration cycle comprises indirectly measuring a momentary lung volume of said subject.

28. A heart stimulator as claimed in claim 25 wherein said respiration cycle comprises at least two stages, each having a different stimulation pulse energy requirement, wherein the step of monitoring said respiration cycle includes generating a signal identifying which stage of said respiration cycle constitutes said current stage, and wherein the step of adapting the energy comprises adapting the energy of a stimulation pulse dependent on the stage of the respiration cycle identified as the current stage.

29. A method as claimed in claim 25 wherein the step of adapting the energy comprises changing an amplitude of a stimulation pulse for adapting the energy of that stimulation pulse to the current stage in the respiration cycle determined by monitoring the respiration cycle.

30. A method as claimed in claim 25 wherein the step of adapting the energy comprises changing a pulse duration of a stimulation pulse for adapting the energy of that stimulation pulse to the current stage in the respiration cycle determined by monitoring the respiration cycle.

31. A method as claimed in claim 25 wherein the steps of emitting successive stimulation pulses comprises emitting successive stimulation pulses each comprised of a stimulation complex of at least two pulses having a timing relation therebetween.

32. A method as claimed in claim 31 wherein the steps of adapting the energy comprises changing the timing relation dependent on the current stage in the respiration cycle determined by monitoring the respiration cycle.

33. A method as claimed in claim 31 wherein the step of adapting the energy comprises changing an amplitude of said pulses dependent on the current stage in the respiration cycle determined by monitoring the respiration cycle.

34. A method as claimed in claim 25 wherein each stimulation pulse having an appropriate energy produces an evoked response in said heart within a response time period following that stimulation pulse, and said method comprising the additional step of detecting whether each stimulation pulse has produced said evoked response within said response time period.

35. A method as claimed in claim 34 wherein the step of adapting the energy comprises increasing the energy of a next stimulation pulse by a predetermined amount relative to an energy of a preceding pulse if said preceding pulse did not produce an evoked response.

36. A method as claimed in claim 34 wherein the step of adapting the energy comprises increasing the energy of a next stimulation pulse by a programmable amount relative to an energy of a preceding pulse if said preceding pulse did not produce an evoked response.

37. A method as claimed in claim 34 wherein the step of adapting the energy comprises increasing the energy of a next stimulation pulse by a predetermined percentage relative to an energy of a preceding pulse if said preceding pulse did not produce an evoked response.

38. A method as claimed in claim 34 wherein the step of adapting the energy comprises increasing the energy of a next stimulation pulse by a programmable percentage relative to an energy of a preceding pulse if said preceding pulse did not produce an evoked response.

39. A method as claimed in claim 34 comprising the additional steps of identifying and storing the energy associated with each stimulation pulse with respect to the stage in the respiration cycle in which that stimulation pulse was emitted, means for storing a stored stimulation pulse energy for each respiration cycle stage and for normally causing each stimulation pulse emitted during a respective respiration cycle stage to have said stored stimulation pulse energy, and decreasing the stimulation pulse energy of a next stimulation pulse by a predetermined amount, thereby emitting a decreased energy pulse, if all of a predetermined number of previous stimulation pulses emitted in previous occurrences of said respective stage have produced an evoked response.

40. A method as claimed in claim 39 wherein the step of adapting the energy comprises successively increasing the energy of respective stimulation pulses, following said decreased energy pulse, by a predetermined amount relative to the energy of said decreased energy pulse, if said decreased energy pulse did not produce an evoked response, until an evoked response, until an evoked response is detected.

41. A method as claimed in claim 34 comprising the additional steps of identifying and storing the energy associated with each stimulation pulse with respect to the stage in the respiration cycle in which that stimulation pulse was emitted, storing a stored stimulation pulse energy for each respiration cycle stage and normally causing each stimulation pulse emitted during a respective respiration cycle stage to have said stored stimulation pulse energy, and means for decreasing the stimulation pulse energy of a next stimulation pulse by a programmable amount, thereby emitting a decreased energy pulse, if all of a programmable number of previous stimulation pulses emitted in previous occurrences of said respective stage have produced an evoked response.

42. A method as claimed in claim 41 wherein the step of adapting the energy comprises successively increasing the energy of respective stimulation pulses, following said decreased energy pulse, by a programmable amount relative to the energy of said decreased energy pulse, if said decreased energy pulse did not produce an evoked response, until an evoked response, until an evoked response is detected.

43. A method as claimed in claim 34 comprising the additional steps of identifying and storing the energy associated with each stimulation pulse with respect to the stage in the respiration cycle in which that stimulation pulse was emitted, storing a stored stimulation pulse energy for each respiration cycle stage and normally causing each stimulation pulse emitted during a respective respiration cycle stage to have said stored stimulation pulse energy, and means for decreasing the stimulation pulse energy of a next stimulation pulse by a predetermined percentage, thereby emitting a decreased energy pulse, if all of a predetermined number of previous stimulation pulses emitted in previous occurrences of said respective stage have produced an evoked response.

44. A method as claimed in claim 43 wherein the step of adapting the energy comprises successively increasing the energy of respective stimulation pulses, following said decreased energy pulse, by a predetermined percentage relative to the energy of said decreased energy pulse, if said decreased energy pulse did not produce an evoked response, until an evoked response, until an evoked response is detected.

45. A method as claimed in claim 34 comprising the additional steps of identifying and storing the energy associated with each stimulation pulse with respect to the stage in the respiration cycle in which that stimulation pulse was emitted, storing a stored stimulation pulse energy for each respiration cycle stage and normally causing each stimulation pulse emitted during a respective respiration cycle stage to have said stored stimulation pulse energy, and means for decreasing the stimulation pulse energy of a next stimulation pulse by a programmable percentage, thereby emitting a decreased energy pulse, if all of a programmable number of previous stimulation pulses emitted in previous occurrences of said respective stage have produced an evoked response.

46. A method as claimed in claim 45 wherein the step of adapting the energy comprises successively increasing the energy of respective stimulation pulses, following said decreased energy pulse, by a programmable percentage relative to the energy of said decreased energy pulse, if said decreased energy pulse did not produce an evoked response, until an evoked response, until an evoked response is detected.

* * * * *